United States Patent [19]

Lavin et al.

[11] Patent Number: 5,772,585

[45] Date of Patent: Jun. 30, 1998

[54] SYSTEM AND METHOD FOR MANAGING PATIENT MEDICAL RECORDS

[75] Inventors: Marianne Lavin, Chicago; Michael Nathan, Highland Park, both of Ill.

[73] Assignee: EMC, Inc, Des Plaines, Ill.

[21] Appl. No.: 706,316

[22] Filed: Aug. 30, 1996

[51] Int. Cl.[6] .............................. A61B 5/02; G06F 17/20; G06F 17/28

[52] U.S. Cl. ......................... 600/300; 600/301; 128/920; 128/923

[58] Field of Search .................................. 128/630, 920, 128/923; 600/300, 301

[56] References Cited

U.S. PATENT DOCUMENTS

| | | |
|---|---|---|
| 4,858,121 | 8/1989 | Barber et al. . |
| 4,893,270 | 1/1990 | Beck et al. . |
| 4,991,091 | 2/1991 | Allen . |
| 5,051,924 | 9/1991 | Bergeron et al. . |
| 5,054,096 | 10/1991 | Beizer . |
| 5,168,548 | 12/1992 | Kaufman et al. . |
| 5,231,670 | 7/1993 | Goldhor et al. . |
| 5,262,943 | 11/1993 | Thibado et al. . |
| 5,267,155 | 11/1993 | Buchanan et al. .................. 364/419.14 |
| 5,287,270 | 2/1994 | Hardy et al. . |
| 5,296,688 | 3/1994 | Hamilton et al. ........................ 235/375 |
| 5,303,148 | 4/1994 | Mattson et al. . |
| 5,319,543 | 6/1994 | Wilheim . |
| 5,327,341 | 7/1994 | Whalen et al. . |
| 5,361,202 | 11/1994 | Doue . |
| 5,365,598 | 11/1994 | Sklarew . |
| 5,390,238 | 2/1995 | Kirk et al. . |
| 5,442,728 | 8/1995 | Kaufman et al. . |
| 5,454,046 | 9/1995 | Carman, II . |
| 5,463,696 | 10/1995 | Beernink et al. . |
| 5,475,798 | 12/1995 | Handlos . |
| 5,477,511 | 12/1995 | Englehardt . |
| 5,481,645 | 1/1996 | Bertino et al. . |
| 5,553,609 | 9/1996 | Chen et al. .............................. 128/630 |
| 5,560,005 | 9/1996 | Hoover et al. .......................... 395/600 |
| 5,640,953 | 6/1997 | Bishop et al. . |

OTHER PUBLICATIONS

Microfiche Appendix, "System and Method for Managing Patient Medical Records", Lavin et al (Source Code).

Hewlett–Packard, *"Patient Data Management System,"* First Edition, Jan. 1982.

AIWEEK, *"Hospital Information Systems Improve Patient Care,"* Dec. 1, 1988.

*Primary Examiner*—William E. Kamm
*Assistant Examiner*—Carl H. Layno
*Attorney, Agent, or Firm*—Brinks Hofer Gilson & Lione

[57] ABSTRACT

A system and method for managing patient medical information to facilitate data management and improve physician access to and recordal of examination data is described. The method comprises a computer aided process including the steps of scheduling appointments, entering and displaying data to a physician, updating the patient data with progress notes concurrently with an examination, displaying allergy warnings and recording a diagnosis based on the progress notes. A common graphic user interface is also disclosed to facilitate operation of the preferred system and method. The system and method are implemented with a relational database operating on data tables which store information input into the user interface.

49 Claims, 17 Drawing Sheets

Microfiche Appendix Included
(10 Microfiche, 916 Pages)

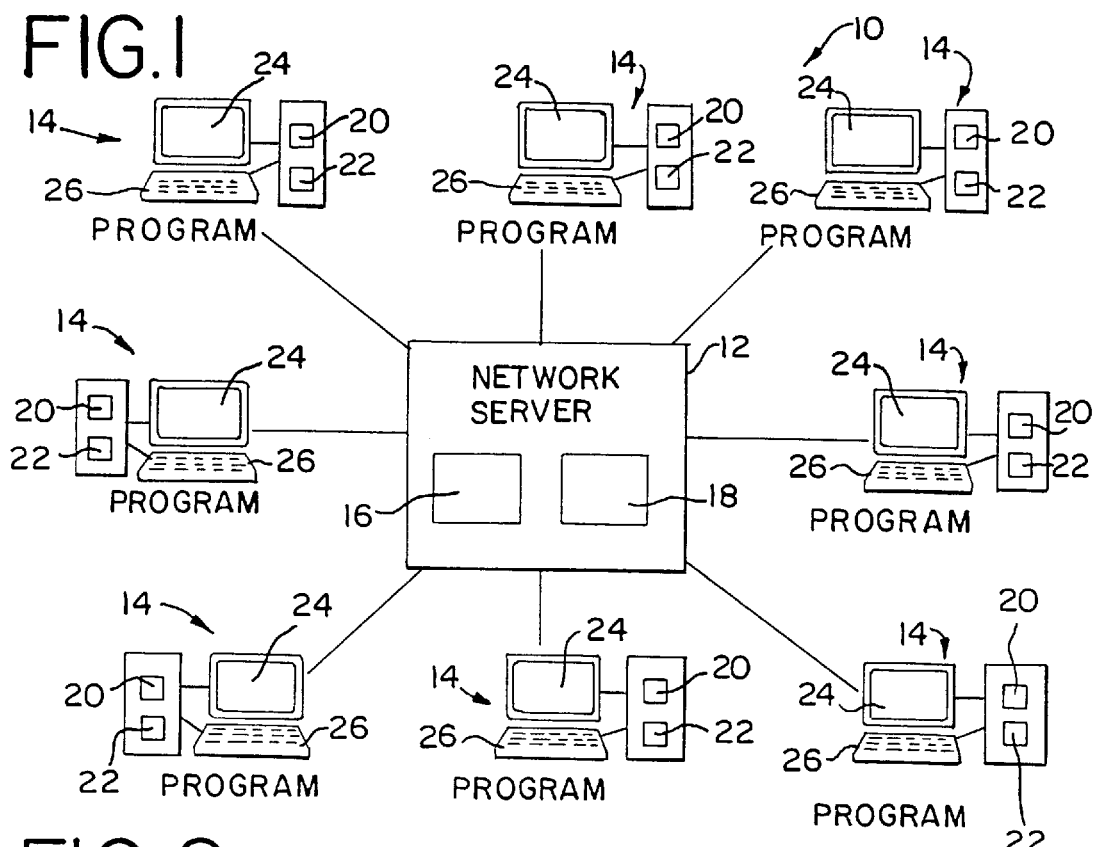
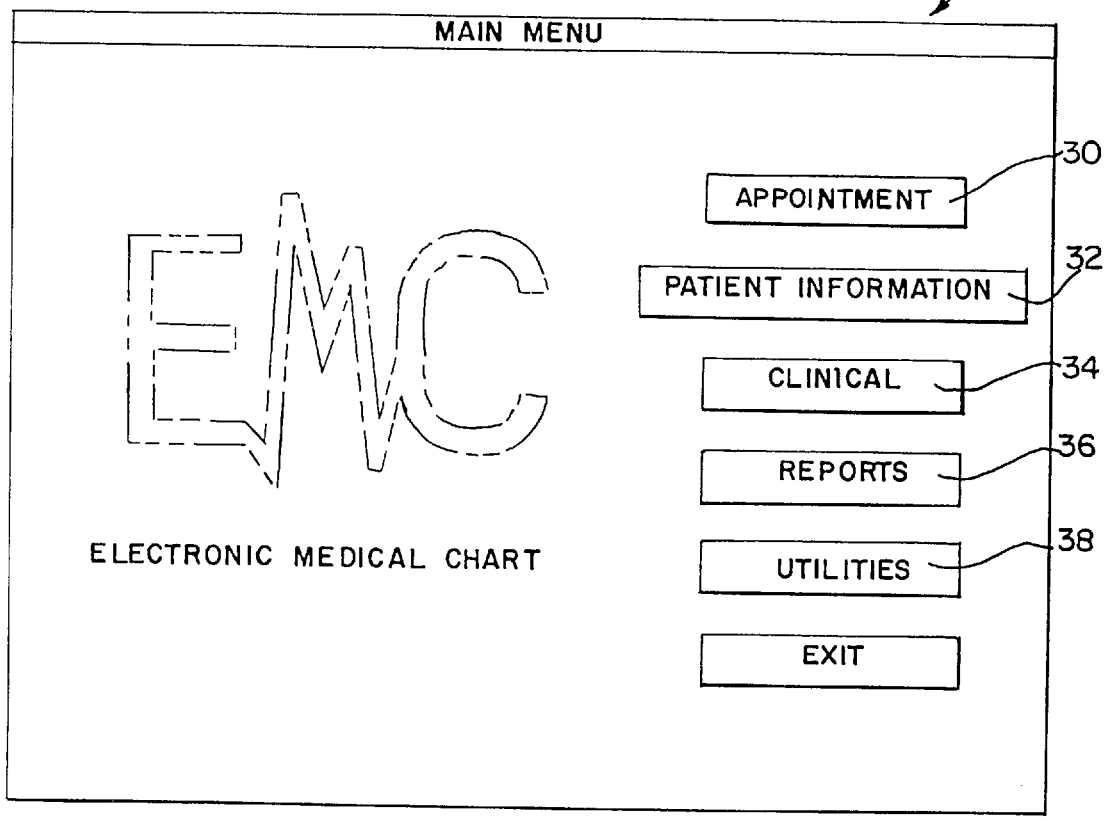

FIG. 4

APPOINTMENTS

| APPOINTMENT | PATIENT | PHYSICIAN |

DOCTOR [CONSULT]  LOCATION [GLENVIEW] — 64

62 — APPOINTMENT

PATIENT [ ] — 66
PHONE(H) ( ) [ ] - [ ]
INSURANCE [ ]
REASON [ ] □Px — 68

[ OK ]  [ CANCEL ]   56

| | 08:00 AM | |
|8a| 08:15 AM | |
|9a| 08:30 AM | |
|10a| 08:45 AM | |
|11a| 09:00 AM | |
|12p| 09:15 AM | |
|1p| 09:30 AM | |
|2p| 09:45 AM | |
|3p| 10:00 AM | |
|4p| 10:15 AM | |
|5p| 10:30 AM | |
|6p| 10:45 AM | |
|7p| 11:00 AM | |
|8p| 11:15 AM | |
| | 11:30 AM | |
| | 11:45 AM | |

AUGUST  1996
| SUN | MON | TUE | WED | THU | FRI | SAT |
|-----|-----|-----|-----|-----|-----|-----|
|     |     |     |     | 1   | 2   | 3   |
| 4   | 5   | 6   | 7   | 8   | 9   | 10  |
| 11  | 12  | 13  | 14  | 15  | 16  | 17  |
| 18  | 19  | 20  | 21  | 22  | 23  | 24  |
| 25  | 26  | 27  | 28  | 29  | 30  | 31  |

58

○BY DOCTOR  ○BY LOCATION  [CANCEL APPT.] [NEW APPT.]

8/14/96 ◊ [ ] ▨AC ◊ 8/14/96
FUEL

| WEEKLY ALL Drs. | WEEKLY GLANCE | PRINT | TO REPORTS | TO MAIN MENU |

APPOINTMENTS

| APPOINTMENT | PATIENT | PHYSICIAN |

LAST NAME [ ] FIRST [ ] MIDDLE INITIAL [ ]

ADDRESS [ ]

CITY [ ]  STATE [ ]  ZIP [ ]   — 172

PHONE(O) [ ] [ ] - [ ] EXT. [ ]  PHONE(H) ( [ ] ) [ ] - [ ]

INSURANCE COMPANY [ ] — 174

PRIMARY PHYSICIAN [ ▼ ] — 176

NOTES [ ] — 178

170

[ADD NEW PATIENT]

| WEEKLY ALL DRS | WEEKLY GLANCE | PRINT | TO REPORTS | TO MAIN MENU |

FIG. 6

APPOINTMENTS

| APPOINTMENT | PATIENT | PHYSICIAN |

DOCTOR: CONSULT

NAME: CONSULT, CONSULT, M.D.

PHONE(O): ( ) -

| AUGUST | | | | | 1996 | |
|---|---|---|---|---|---|---|
| SUN | MON | TUES | WED | THU | FRI | SAT |
| | | | | 1 | 2 | 3 |
| 4 | 5 | 6 | 7 | 8 | 9 | 10 |
| 11 | 12 | 13 | 14 | 15 | 16 | 17 |
| 18 | 19 | 20 | 21 | 22 | 23 | 24 |
| 25 | 26 | 27 | 28 | 29 | 30 | 31 |

[ON/OFF] [DELETE ON/OFF] [8/14/96] [8/14/96]

DOCTOR AVAILABLE TIME LIST

| DAY | BEGIN | END | LOCATION |
|---|---|---|---|
| WEDNESDAY | 5:00.00 PM | 7:00.00 PM | GLENVIEW |

[ADD] [DELETE]   94

8/14/96

| 08:00 AM | |
| 08:30 AM | |
| 09:00 AM | |
| 09:30 AM | |
| 10:00 AM | |
| 10:30 AM | |
| 11:00 AM | |
| 11:30 AM | |
| 12:00 PM | |
| 12:30 PM | |
| 01:00 PM | |
| 01:30 PM | |
| 02:00 PM | |
| 02:30 PM | |
| 03:00 PM | |
| 03:30 PM | |
| 04:00 PM | |
| 04:30 PM | |
| 05:00 PM | GLEN |
| 05:30 PM | |
| 06:00 PM | |
| 06:30 PM | |
| 07:00 PM | |

[WEEKLY ALL DRS.] [WEEKLY GLANCE] [PRINT] [TO REPORTS] [TO MAIN MENU]

FIG. 6A

WEEKLY APPOINTMENT GLANCE

| DOCTORS | 9/2/96 MON | 9/3/96 TUE | 9/4/96 WED | 9/5/96 THU | 9/6/96 FRI | 9/7/96 SAT | 9/8/96 SUN | |
|---|---|---|---|---|---|---|---|---|
| | | | | | | | | 8AM |
| | | | | | | | | 9AM |
| | | | | | | | | 10AM |
| | | | | | | | | 11AM |
| | | | | | | | | 12PM |
| | | | | | | | | 1PM |
| | | | | | | | | 2PM |
| | | | | | | | | 3PM |
| | | | | | | | | 4PM |
| | | | | | | | | 5PM |
| | | | | | | | | 6PM |
| | | | | | | | | 7PM |

[VIEW MORE] [EXIT]

FIG. 7

PATIENT INFORMATION

| PATIENT | INSURANCE | EMPLOYER | FAMILY | HISTORY | VITAL SIGNS |

- ACCOUNT. NO. [        ]   CAP NO. [       ]   SSN [   ]-[  ]-[    ]
- LAST NAME [        ]   FIRST [        ]   MIDDLE INITIAL [   ]
- STREET [                                    ]
- CITY [            ]   STATE [   ]   ZIP CODE [      ]
- PHONE(H) ( [   ] ) [   ]-[    ]   BIRTHDATE [  ]/[  ]/[  ]   AGE [   ]
- PHONE(O) ( [   ] ) [   ]-[    ]
- SEX:  o MALE   o FEMALE
- MARITAL:  o SINGLE  o SEPARATED  o MARRIED  o DIVORCED  o WIDOWED
- OCCUPATION [            ]
- REFERRING PHYSICIAN [            ]

| NEW | EDIT | TO MAIN MENU |

PATIENT INFORMATION

| PATIENT | INSURANCE | EMPLOYER | FAMILY | HISTORY | VITAL SIGNS |

─── FILL IN ONLY IF THE PATIENT IS NOT A POLICYHOLDER ───

- INS. ID [        ]   TELEPHONE [        ]
- LAST NAME [        ]   FIRST [        ]   MIDDLE INITIAL [   ]
- STREET [                                    ]
- CITY [            ]   STATE [   ]   ZIP CODE [      ]

}82

─── INSURANCE COMPANY INFORMATION ───

- NAME [                            ]
- STREET [                          ]
- CITY [            ]   STATE [   ]   ZIP CODE [      ]
- TELEPHONE [       ]   POLICY NO. [       ]   GROUP NO. [       ]

}80

| KAT, KITTY | NEW | EDIT | TO MAIN MENU |

FIG. 9

PATIENT INFORMATION

| PATIENT | INSURANCE | EMPLOYER | FAMILY | HISTORY | VITAL SIGNS |

─ EMPLOYER INFORMATION ─

NAME [ ]
STREET [ ]
CITY [ ]  STATE [ ]  ZIP CODE [ ]
TELEPHONE [ ]

} 84

─ GUARANTOR INFORMATION ─

LAST NAME [ ]  FIRST [ ]  MIDDLE INITIAL [ ]
STREET [ ]
CITY [ ]  STATE [ ]  ZIP CODE [ ]
PHONE [ ]  SSN [ ]  RELATION [ ]

} 86

KAT, KITTY | NEW | EDIT | TO MAIN MENU

PATIENT INFORMATION 112

| PATIENT | INSURANCE | EMPLOYER | FAMILY | HISTORY | VITAL SIGNS |

118

RELATIONS

NAME

DISEASE LIST
ABDOMINAL PAIN
ABO HEMLYTIC DISEASE
ABSCESS/CELLULITIS
ACNE
ACUTE RENAL FAILURE
ADENITIS
ADENOPATHY/ADENITIS

114

[ADD NEW MEMBER] [DELETE MEMBER]

RELATION   NAME                    DISEASE

120

KAT, KITTY | NEW | EDIT | TO MAIN MENU

FIG. 11

PATIENT INFORMATION

| PATIENT | INSURANCE | EMPLOYER | FAMILY | HISTORY | VITALSIGNS |

PAST MEDICAL HISTORY

DISEASE LIST
- ABDOMINAL PAIN
- ABO HEMLYTIC DISEASE
- ABSCESS/CELLULITIS
- ACNE
- ACUTE RENAL FAILURE

106

[ADD]
[REMOVE]

SELECTED ILLNESS/SURGERIES — 108

DATE (M/D/YY) — 110

| DATE | DISEASE |

100
104

HABITS — 102

☐ SMOKE
☐ ALCOHOL
☐ COFFEE
☐ EXERCISE

KATY, KITTY    NEW | EDIT | TO MAIN MENU

FIG. 12

PATIENT INFORMATION

| PATIENT | INSURANCE | EMPLOYER | FAMILY | HISTORY | VITAL SIGNS |

[ADD]  124    126   DATE
HEIGHT  /      WEIGHT  LBS. OZ.   HEAD   CM — 132
TEMP — 128    PULSE — 130    RESPIRATION
         134
B.P. SUPINE         SITTING — 136

122

CHIEF COMPLAINT — 138

DRUG ALLERGIES — 140

OTHER ALLERGIES — 142

KAT, KITTY    NEW | EDIT | TO MAIN MENU

FIG. 14

| CLINICAL | | | | | |
|---|---|---|---|---|---|
| PATIENT | VITAL SIGNS | PROGRESS | DIAGNOSIS | PRESCRIPTION | VACCINE |

NAME [KAT, KITTY]

SSN [ ]   SEX [F]

BIRTHDATE [6/8/57]   AGE [39Y]

REFERING [ ]

ADDRESS

PHONE(H)

ALLERGIES
DRUG ALLERGIES
PENICILLIN

HABITS
☐ SMOKE
[MORE]

FAMILY HISTORY

| RELATION | NAME OF MEMBER | NAME OF DISEASE/PROCEDURES |
|---|---|---|
| | | |
| | | |

180

| KAT, KITTY | F | 39Y | EMC | ☒ ALLERGIES | TO PATIENT INFOR. | TO MAIN MENU |

FIG. 15

| CLINICAL | | | | | |
|---|---|---|---|---|---|
| PATIENT | VITAL SIGNS | PROGRESS | DIAGNOSIS | PRESCRIPTION | VACCINE |

TEST RESULT — 192   DATE [ ]

HEIGHT [ ]' [ ]/[ ]"   WEIGHT [ ] LB. [ ] OZ.   HEAD [ ] CM.

TEMPERATURE(F) [ ]   PULSE(I/MIN) [ ]   RESPIRATION(I/MIN) [ ]

BLOOD PRESSURE
SUPINE [ ]   SITTING [ ]

CHIEF COMPLAINT

[SORT/DATE]  [SORT/DIAG] 196   HEALTH HISTORY

| DATE | N/R | DIAGNOSIS | PROCEDURE |
|---|---|---|---|
| | | | |
| | | | |
| | | | |
| | | | |

190

194

| KAT, KITTY | F | 39Y | EMC | ☒ ALLERGIES | TO PATIENT INFO. | TO MAIN MENU |

FIG. 16

| CLINICAL | | | | | |
|---|---|---|---|---|---|
| PATIENT | VITAL SIGNS | PROGRESS | DIAGNOSIS | PRESCRIPTION | VACCINE |

CHIEF COMPLAINT — 202

SUBJECTIVE

OBJECTIVE: — 204

200

ASSESSMENT: — 206

PLAN: — 208

| HAND WRITING | TEST | VOICE | ADD PX | VIEW PX | |
| KAT, KITTY 210 | F | 39Y | EMC | ☒ ALLERGIES | TO PATIENT INFO. | TO MAIN MENU |

| PHYSICAL EXAM | | | |
|---|---|---|---|
| OBJECTIVE | SUBJECTIVE | VITALS | |

| OBJECTIVE | NORMAL | COMMENT |
|---|---|---|
| HEENT | ▨ | |
| NECH/THYROID | | |
| LUNGS | | |
| BREASTS | | |
| HEART | | |
| ABD | | |
| GU | | |
| SKELETAL | | |
| SCOLIOSIS | | |
| SKIN | | |
| NEURO | | |

215

216    217    218

SAVE    CANCEL

FIG. 16B

PHYSICAL EXAM —220

| OBJECTIVE | SUBJECTIVE | VITALS —221 |
|---|---|---|

| SUBJECTIVE | COMMENT |
|---|---|
| MEDICAL CONDITION | ///////////// |
| MEDICATIONS | |
| RECENT MEDICAL | |
| SCHOOL | |
| ACTIVITES | |
| SOCIAL | |
| TOBACCO | |
| ALCOHOL | |
| DRUGS | |
| DEPRESSION | |
| MENSTRUAL HISTORY | |
| SEXUAL CONTACT | |
| R.O.S | |
| INJURY | |

}—219

[SAVE] [CANCEL]

FIG. 16C

PHYSICAL EXAM

| OBJECTIVE | SUBJECTIVE | VITALS |
|---|---|---|

[ADD]       |◄ ◄ ► ►|  DATE [        ]

HEIGHT [ ]' [ ][ ] / [ ]"    WEIGHT [ ][ ][ ] LBS. [ ] OZ.    HEAD [ ][ ][ ] CM.

TEMP [ ][ ][ ][ ]    PULSE [ ][ ][ ]    RESPIRATION [ ][ ]

B.P. SUPINE [ ][ ][ ][ ][ ][ ]    SITTING [ ][ ][ ][ ][ ][ ]

CHIEF COMPLAINT [                              ]

—223
—222
—224

DRUG ALLERGIES [                              ]

OTHER ALLERGIES [                              ]

}—225

[SAVE] [CANCEL]

FIG. 17

CLINICAL

| PATIENT | VITAL SIGNS | PROGRESS | DIAGNOSIS | PRESCRIPTION | VACCINE |

| DIAGNOSIS | PROCEDURE | FREE |
|---|---|---|
| | | |

[DELETE]  [DELETE]

INSURANCE INFOR.  COMPANY:  LAB:

[OTHERS] [NEW]     [OTHERS] [NEW]

KAT, KITTY | F | 39Y | EMC | | TO PATIENT INFO. | TO MAIN MENU

FIG. 19

CLINICAL

| PATIENT | VITAL SIGNS | PROGRESS | DIAGNOSIS | PRESCRIPTION | VACCINE |

ALLERGIES

℞ AMOXICILLIN

250 MG CAPSULE

DOSAGE

☐ LABEL    REFILL TIMES

☐ MAY SUBSTITUTE  ☐ MAY NOT SUBSTITUTE

INSTRUCTION

| I P.O.T.I.D. x 10 DAYS
| QID
| Tsp. T.I.D. x 10 DAYS
| 1-2 DROPS ON AFFECTED EAR PRN.

SIGNATURE                M.D.

[CANCEL] [SAVE]

KAT, KITTY | F | 39Y | EMC | | TO PATIENT INFOR | TO MAIN MENU

FIG. 20

| CLINICAL | | | | | |
|---|---|---|---|---|---|
| PATIENT | VITAL SIGNS | PROGRESS | DIAGNOSIS | PRESCRIPTION | VACCINE |

| VACCINE ADMINISTRATION RECORD |
|---|

| VACCINE | DATE M/D/Y | AGE | SITE | VACCINE MANUFACTURER | VACCINE LOT NUMBER | HANDOUT PUBL. DATE | INITIALS | SIGNATURE OF PARENT OR GUARDIAN |
|---|---|---|---|---|---|---|---|---|
| | | | | | | | | |

270

| NEW RECORD | PRINT VACCINE | | LAB | DONE |
|---|---|---|---|---|
| KAT, KATY | F | 39Y | EMC | TO PATIENT INFOR. | TO MAIN MENU |

FIG. 20A

EMC

LAB RECORD

PATIENT KAT, KITTY

| NAME | DATE M/D/Y | HB/HT | WBC | POLY | LYM | PLTS | RAPID | 24 HR. | SP. GR | PH | BLD | PROT. | GL. |
|---|---|---|---|---|---|---|---|---|---|---|---|---|---|
| | | | | | | | | | | | | | |

| NEW TEST | | EXIT |
|---|---|---|

FIG. 21

ALPHABETICAL LISTING OF TABLES

- APPOINTMENTS — 302
- ALLERGIES — 304
- CANCEL_APNTMTS — 306
- CUSTOM_D LIST — 308
- CUSTOM_P LIST — 310
- DIAG_HIST — 312
- DIAG_REF — 314
- DOC_ONOFF — 316
- DOC_REF — 318
- DOCTOR_AVAILTIME — 320
- DOSAGE — 322
- EMPLOYER_INFOR — 324
- FAMILY_HIST — 326

- FAMILY_MEMBER — 328
- FOLLOW_UP_NOTES — 330
- GUARANTOR_INFOR — 332
- HABITS — 334
- INS_INFOR — 336
- INSTRUCTION — 338
- INS_LAB — 340
- LAB — 342
- LAB_REPORT — 344
- LAB_TEST — 346
- LOCATIONS — 348
- OBJECTIVE — 350
- OBJ_NAME — 352

- PATIENT_INFOR — 354
- PRESCRIPTION — 356
- PROC_HIST — 358
- PROC_REF — 360
- PROG_INDEX — 362
- PROGRESS — 364
- REGINFOR — 366
- REPORT_INFO — 368
- SUBJECTIVE — 370
- SUBNAME — 372
- USER_INFO — 374
- VACCINE — 376
- VITALS — 378
- WEEK_DAY — 380

FIG. 22    APPOINTMENTS TABLES/RELATIONSHIPS
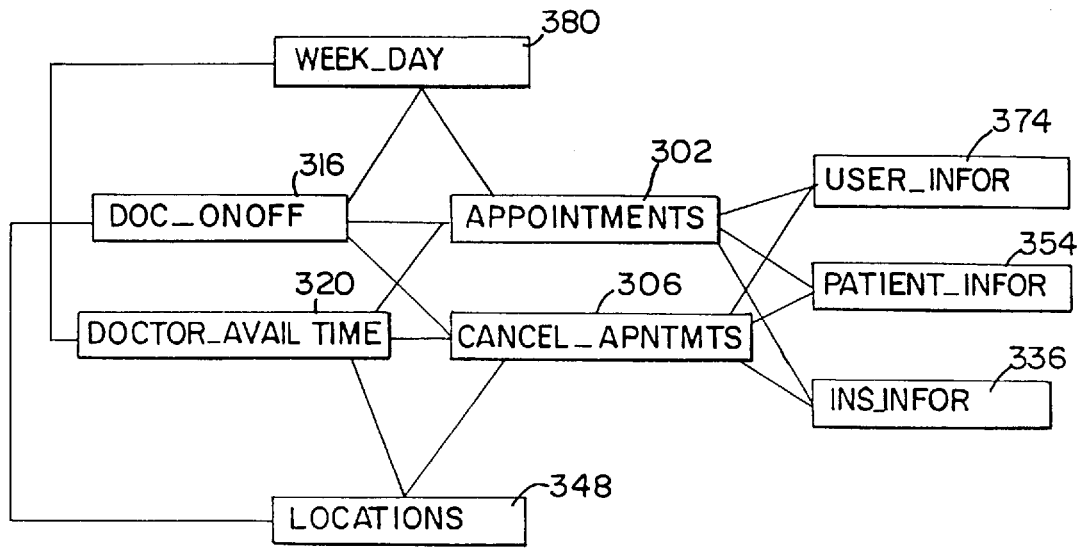
FIG. 23    PATIENT INFORMATION TABLE/RELATIONSHIPS
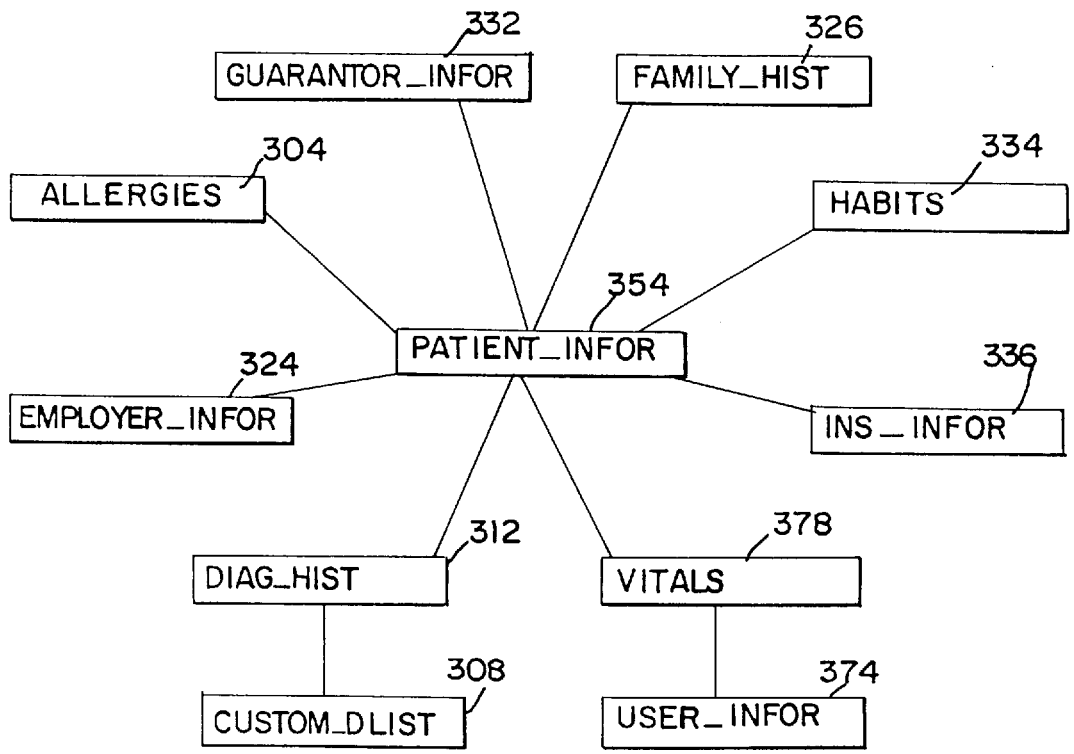

SYSTEM AND METHOD FOR MANAGING PATIENT MEDICAL RECORDS

MICROFICHE APPENDIX

A Microfiche Appendix of the presently preferred source code is attached and comprises 10 sheets, having a total of 916 frames. The Microfiche Appendix contains material which is subject to copyright protection. The copyright owner has no objection to the facsimile reproduction by anyone of the Microfiche Appendix, as it appears in the Patent and Trademark Office patent files or records, hut otherwise reserves all copyright rights whatsoever.

BACKGROUND OF THE INVENTION

This invention relates to a system and method for managing patient medical information. More particularly, this invention relates to a system and method for improving medical clinic information management and examination information handling.

Medical clinics generally process patient scheduling, medical history, billing, and clinical information in discrete ways. Typically, clinical examination notes and patient charts are kept in meticulously maintained paper files using standard paper charting techniques. Information relating to the patient of a particular physician or clinic is often kept in several places. Further, the use of paper charting results in many storage and retrieval challenges. Physicians will sometimes dictate segments or summaries of patient examinations for later transcription by secretaries into a computer database. This process is time consuming and inefficient.

The various available methods and systems for recording and manipulating different types of patient information are typically limited to discrete computer programs or handwritten methods. Meaningful manipulation of patient information on a clinical basis, or even by physician, can be difficult due to differing locations of the information and various formats used to store the information. The information required for each of the separate data files of these computer programs may overlap and lead to redundant data entry tasks being performed. The tasks that may be performed on various separate electronic databases often require learning to operate different user interfaces. Additionally, many clinics operating under health maintenance organization (HMO) oversight are required to audit the examination notes of physicians for consistency and trends in diagnoses and treatment. The lack of computerized databases for monitoring and updating clinical examination data and the time consuming process of retranscribing and editing paper charts into a computer database, can complicate this auditing process.

Accordingly, there is a need for a comprehensive system and method of managing patient scheduling, insurance, clinical examination, billing, and prescription information. Such a system would have a common user interface to allow different medical personnel access to centralized files regarding patients. It would be advantageous to have a method for concurrently recording examination and diagnoses notes in a database during patient examination. Further, a common graphic user interface capable of accessing all necessary tasks through a common database structure would be advantageous.

SUMMARY OF THE INVENTION

The present invention provides for a comprehensive method of managing and manipulating clinical medical information for use by medical professionals. One aspect of the present invention includes a method for creating, managing, updating and analyzing patient information in a medical database on at least one computer having a processor, a data entry device, a memory, and a display. A medical professional compiles a database of patient data including demographic, insurance, and billing information. A receptionist may schedule patient appointments and automatically generate reminders. Nurses and physicians can then enter patient medical history and vital statistics data during a patient office visit into a common relational database. Medical alerts are displayed to warn of allergies the patient may have. A physician may update progress notes during a patient examination by entering in subjective data, objective data, assessments and treatment plan data via a graphic user interface on a computer in the examination room. Preferably, the physician may enter examination data via a voice input device, a computer pen or a keyboard. The examination data may be left as handwriting digitally stored or translated into text from the detected handwriting when a computer pen is used. The date may also be translated into text and stored as text from voice input.

According to another aspect of this invention a medical information system for managing patient medical history and examination data is provided. The system includes a processor, a display in communication with the processor, memory in communication with the processor for storing and manipulating patient data, and an input device such as a keyboard, computer pen or microphone for receiving patient data. The processor preferably includes patient identification means for responding to information entered at the input device and accessing a particular patient's datafile from the memory. Also, the processor has patient examination means to receive and display patient data to a physician during an office visit. The patient examination means preferably include an allergy warning mechanism that retrieves allergy information for the particular patient and displays an allergy warning on the display.

Another aspect of the present invention is a graphic user interface, displayed on a computer display device, for use in storing and retrieving patient medical information held in a database. The graphic user interface consists of a main menu screen having a plurality of function buttons for selecting one of a predetermined number of patient medical information screens. The function buttons include appointment, patient information, clinical, report and utilities buttons. An appointment screen is accessible via the appointment button. A patient information interface is accessible via the patient information button. A user may also access either a clinical examination interface accessible or a reports screen accessible via the clinical, utilities or reports buttons, respectively.

Another aspect of the present invention is a relational database including a set of data tables associated with the above system and interface. The tables store the information entered by the system user, and the relationships among various tables allows the user to retrieve and manipulate the stored information in a variety of ways. For example, a particular table may point to another table to allow the user to retrieve the data from both tables and analyze the relationship or association between both sets of data. This gives the physician, insurer, or other health care provider the unique ability to examine the efficacy of medical procedures, diagnoses, prescriptions, costs or other variables within a particular practice groups.

Another advantage of the presently preferred embodiments is that multiple items of information, previously recorded on separate paper and electronic media, may now be accessed and entered at the common user interface and database structure simultaneously by more than one user. In addition to the elimination of redundant data entry and centralization of patient information, another advantage of the presently preferred embodiment is the ability for physicians to record patient examination data concurrently with examination through a variety of convenient methods. Not only is a physician aided by the ability to record examination, conclusions, and observations while they are still fresh, but clinical staff and auditors can quickly and easily review these electronically recorded patient examination notes.

BRIEF DESCRIPTION OF THE DRAWINGS

FIG. 1 is a computer network suitable for use with the presently preferred embodiment.

FIG. 2 is a main menu screen display.

FIG. 4 is an appointment schedule display.

FIG. 5 is a patient selection/information display.

FIG. 6 is a clinic scheduling display.

FIG. 6A is a weekly schedule display.

FIG. 7 is a patient information display.

FIG. 8 is a patient insurance display.

FIG. 9 is a patient employer display.

FIG. 10 is a patient family medical history display.

FIG. 11 is a patient medical history display.

FIG. 12 is a vital statistics display.

FIG. 14 is a patient selection and demographic display showing clinical aspects.

FIG. 15 is a patient vital signs display in the clinical module.

FIG. 16 is a progress notes display in the clinical module.

FIG. 16A is an objective information screen in the physical exam display accessible via the progress notes display of FIG. 16.

FIG. 16B is a subjective information screen in the physical exam display accessible via the progress notes display of FIG. 16.

FIG. 16C is a vital statistics information screen in the physical exam display accessible via the progress notes display of FIG. 16.

FIG. 17 is a diagnosis display.

FIG. 19 is a preferred prescription display.

FIG. 20 is a vaccine display.

FIG. 20A is a lab record display.

FIG. 21 is an alphabetical listing of database tables.

FIG. 22 is a map of the relationships among various database tables in the appointment modules associated with FIGS. 3–6.

FIG. 23 is a map of the relationships among various database tables shown in FIG. 21.

DETAILED DESCRIPTION OF THE PRESENTLY PREFERRED EMBODIMENTS

Figure 3:
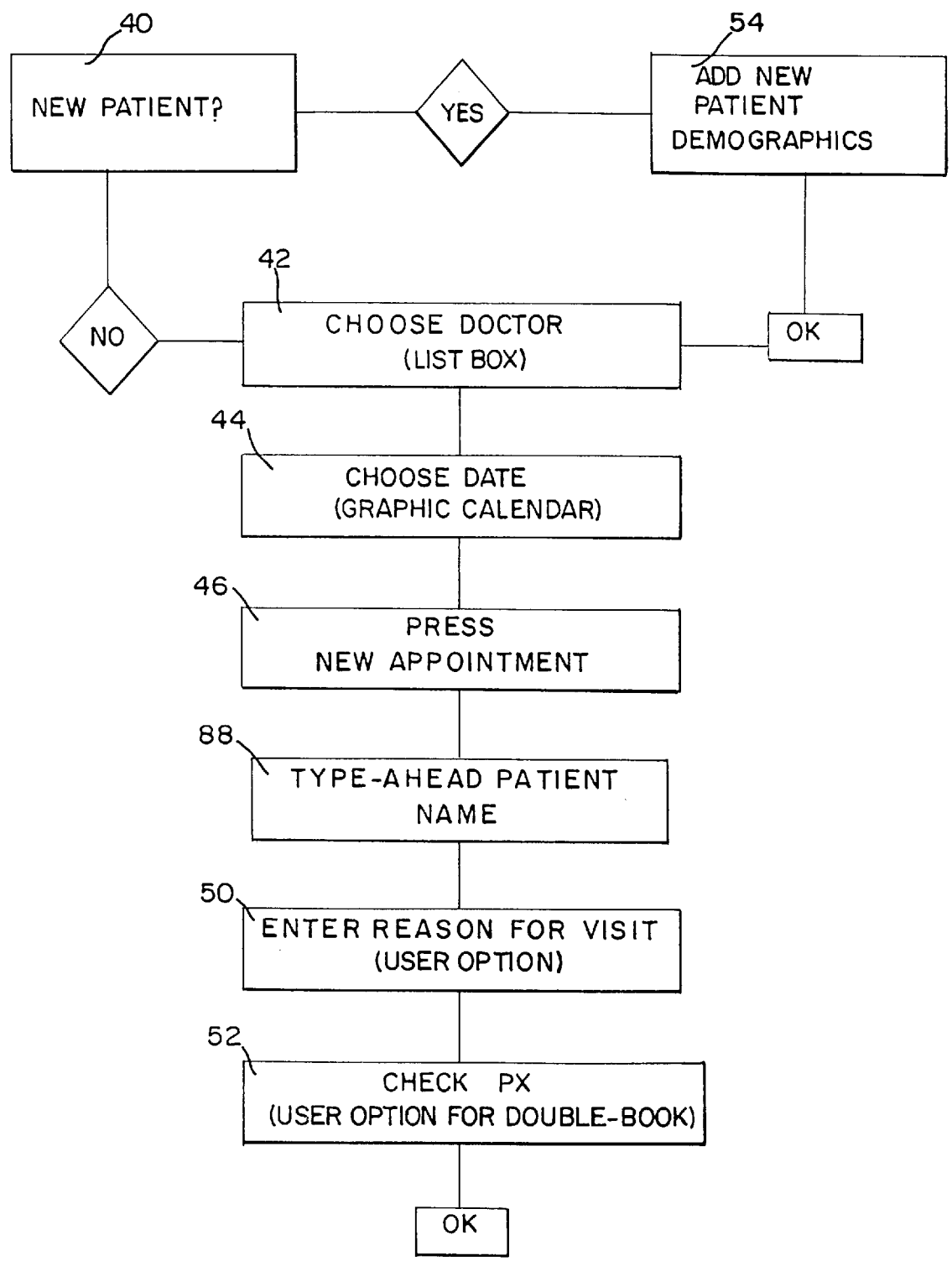
FIG. 3 is a flow chart illustrating one preferred method of scheduling patient appointments.

According to a presently preferred embodiment, a new and improved method for managing and processing patient medical information in a medical clinic environment is provided. The present method links together multiple tasks and information pools formerly kept in separate locations and having limited accessibility. The present method accomplishes ease of management for patient medical information by using convenient flexible appointment scheduling and medical history recording steps with a common graphic user interface. Multiple clinic personnel and physicians may access various aspects of common database information regarding a specific patient or a group of patients. Physician examination is expedited and improved with electronic recordal of information presently performed through paper charting. Further, the presently preferred method informs patients and medical practitioners of existing patient medication or allergy problems. Traditionally, the presently preferred method accommodates multiple methods for inputting information into an electronic relational database.

The relational database used to store, manipulate and retrieve the information herein can be implemented on a variety of commercially available database authoring packages. In the preferred embodiment, information is organized into categorical tables associated with the various input screens described below. The tables described below are listed by their table names in FIG. 21, and are referenced by numerals having "3" as a first digit. Preferably, these tables are implemented with a variety of cross-referencing or pointing relationships, with some tables pointing to several other tables. This allows the user to retrieve information in a variety of formats in order to better utilize the information contained in the database. The tables and their relationships will be described in more detail below, after a discussion of the system components and information entry screens.

Turning now to the first page of the drawings, a computer system 10 which is suitable for use with the presently preferred method, is shown in FIG. 1. The system 10 includes a server 12 and at least one work station 14. The server 12 contains memory 16 and a processor 18 for retaining a common database and manipulating patient information in accordance with requests from each of the work stations 14. Each work station 14 preferably has memory 20, a processor 22, a display 24, and a data entry device 26.

Each work station 14 is capable of executing a computer program and reading and writing to and from its memory 20. The work stations 14 in the system 10 may be fixed or portable personal computers adapted to operate in communication with the server 12. In a preferred embodiment, the system may simply comprise a single personal computer suitable for executing computer programs and processing data information input to the computer. Suitable hardware for the system 10 as shown in FIG. 1 is a Compaq Prolinea 300 server, manufactured by Compaq, Inc., having 32 megabytes of memory and a 1 gigabyte hard disk drive. Portable computers such as the IBM ThinkPad 750P, may be implemented as the work stations 14. The network server and work stations preferably utilize processors capable of executing the software in the attached Microfiche Appendix. Network communications may be controlled using commonly available software as is available from Novell, Inc.

The software disclosed in the attached microfiche appendix is preferably written in Visual Basic available from Microsoft Corporation. The graphic user interface implemented in the system and method described below may be formed from software tool kits such as Calendar Widgets™ available from Sheridan Incorporated, TruGrid™ available from Apex, and Schedule VBX available from ADDSoft, Inc. A preferred database tool kit is Microsoft Access from Microsoft Corporation. A presently preferred software embodiment executable on a system such as shown in FIG. 1 is included in the attached Microfiche Appendix. As will be readily apparent to those of ordinary skill in the art, other hardware configurations may be used to implement the preferred software embodiment.

In addition to the computer hardware described above, several alternate data entry input devices may be used along with associated software drivers. For example, data may be entered on a work station 14 using a pen-to-text data entry device and software driver. A suitable computer pen is the IBM ThinkPad Untethered Stylus available from IBM Corporation using IBM Corporation software. Handwriting may also be directly digitally stored according to a preferred embodiment, again using a computer pen such as described above and utilizing Visual Basic software available from Microsoft Corporation. Finally, a third alternative data entry technique available for use according to a presently preferred embodiment is voice-to-text. Preferably the work stations 14 can each possess the capability of receiving a microphone as the data entry device and translating the microphone input into textual material. Any of a number of commonly known microphones may be used to connect with the work station 14, in cooperation with IBM VoiceType dictation software, to translate voice dictated information into textual information for storage and retrieval from memory 20.

It should be understood that the presently preferred embodiment is not limited to execution on the specific computer network and operating system shown and described. Other data processing systems may be used. It should also be understood that the computer programming languages are not limited to those described above, and that any number of known computer languages may be utilized to implement the presently preferred method.

A presently preferred embodiment is typically operated in a medical clinic environment where medical practitioners and staff require access to various types of information previously recorded about existing patients and also require the ability to add new patients to the clinic's files. Every user of the system 10 enters a user name and a password to access information as a security measure, and different levels of data access can be granted to different users. The information relating to the security measures is stored in the relational database in a User Information table, or namely "User_Infor" table 374 (in FIG. 21).

As shown in FIG. 2, when a user first accesses the system, a main menu display 28 will present the user with several options. The user selects the desired task through the data entry device 26. The main menu display includes an appointment button 30, a patient information button 32, a clinical button 34, a reports button 36 and a utilities button 38. Each of these command buttons permits the user to enter a specific group of data entry and retrieval screens for managing and processing patient information.

Preferably, the system utilizes object-oriented programming such that users are not limited to a fixed hierarchy of steps. In this regard, the user may select necessary tasks in any order desired. As shown in FIG. 3, clinical staff may enter information regarding appointment scheduling for physicians and patients. A clinic receptionist receiving a request to make an appointment with a physician will first determine if the patient is new (at step 40). If the patient is an existing patient then the user selects the patient's physician to pull up that physician's appointment schedule (at step 42). The user then may select an available date and time (at step 44). After entering the physician and date, the user presses a new appointment button and enters a patient's name. (At steps 46, 48). In order to expedite entry of patient names in a potentially large database of existing patients, a type-ahead feature is available to narrow down the list of names presented to the user as each letter of the patient's name is typed in.

When the appropriate patient's name, along with all information associated with that patient, has been retrieved, the user may then enter the reason for a visit into the database associated with the patient's name and appointment date (at step 50). The user then has the option to schedule a routine physical examination (at step 52). If the user determines that the patient is not an existing patient, new patient information may then be entered in other screens accessible through the display using buttons on the graphic user interface (at step 54).

FIG. 4 illustrates a preferred appointment screen 56 presented when a user first chooses the appointment button 30 from the main menu display 28. The user may select to view available appointment slots by physician or by location. The appointment screen is associated with various tables including the "Appointments" table 302 and "Cancel_Apntmts" table 306. The screen 56 includes a monthly calendar 58 that allows the user to select a desired day and automatically pull appointment schedules for that selected day. Once a particular day has been selected the processor 22 reveals the appointment schedule list 60 to the user via the display 24 showing the available and scheduled times for the selected physician or location. The appointment screen also includes a physician menu 62 and a location menu 64 that cooperate with the daily appointment schedule list and month selections to show availability of the desired physician or physicians at a desired location. When a satisfactory appointment time and location have been identified, the user will then type in the patient's name in a text box 66, which is associated with Patient Information table 354. The processor 22 automatically retrieves the patient's phone number and insurance information after entering the patient's name if the patient is an existing patient. The user then enters a reason for the visit in a text box 68 specifically dedicated to a description of the patient's present ailment. The appointment is then officially entered by depressing the OK button on the appointment screen 56.

Referring now to FIG. 5, a patient selection screen 170 is presented. The user preferably enters the patient's last name in the address book portion 172 of the patient selection screen 170. A text field provided for a patient's last name includes a pulldown menu 173 that cooperates with a type-ahead function to permit quick access to a patient's file with each additional letter typed into the last name text field. When a patient's last name has been entered, the processor 22 retrieves any known information on the patient from memory and displays it on the selection screen. This information includes insurance company name, primary physician, and notes on items such as patient scheduling 174, 176, 178.

FIG. 6 illustrates another aspect of the appointment scheduling routine of the presently preferred method. As shown in FIG. 6, a physician scheduling screen 88 provides a user with the ability to view and alter physician availability. The scheduling screen 88 places information into the tables relating to physician availability, including the "Doc_OnOff" table 316 and "Doctor_AvailTime" table 320 (tables shown in FIGS. 21–24). As with the patient scheduling, the physician's scheduling screen 88 includes a calendar 90 displaying one month to the user wherein the user can select a specific day to view more detail. A daily appointment scheduler 92 displays the available times and other information for a selected physician in the physician available time list 94. Routines are utilized which keep track of the regular and alternately scheduled days a particular physician is on or off call or at the office. These routines do not allow an appointment with a particular doctor to be scheduled if the doctor is not otherwise scheduled to be in the office. The physician scheduling screen 88 can also call a routine through the "Weekly Glance" button 91 to generate a weekly time schedule showing various doctors, as shown in FIG. 6A.

FIGS. 7–9 illustrate graphic user interface data entry screens displayed on the display 24 when new patient information is entered or when an existing patient's information is recalled. The various patient screens are associated with the Patient Information table 354 ("Patient_Infor") in the relational database (shown in FIGS. 21–24). Referring now to FIG. 7, text boxes for receiving a patient's name, social security number, address and telephone information are shown. Other demographic information such as sex, marital status, age and occupation also accounted for in the screen of FIG. 7. The demographic information screen of FIG. 7 also includes a space 93 for recording the referring physician of the patient.

FIG. 8 illustrates the insurance information screen provided to a user for entering or viewing patient insurance information. The patient information screen includes an insurance company text entry area 80. The insurance information screen is associated with tables in the relational database called "Ins Lab" 340 and "Ins_Infor" 336 (shown in FIGS. 21–24). The insurance company name, policy number and group number may be recorded or retrieved in this portion of the user interface. An uninsured patient text information area 82 is also included on the insurance information screen. FIG. 9 also illustrates another demographic information entry and retrieval screen. This screen permits the user to enter text information on the patient's employer or guarantor through the data entry device 26 of the work station. The employer information screen of FIG. 9 is displayed on the work station display 24 and includes an area 84 for entering employer information and an area 86 for entering guarantor information. These entry areas are associated with an Employer Information table 324 ("Employer_Infor") and a Guarantor Information table 332 ("Guarantor_Infor") (shown in FIGS. 21–24).

FIGS. 10 and 11 illustrate preferred user interface screens for entering patient medical background information. These screens and the database tables associated with them may be accessed through the main menu screen 28 using the patient information button 32 or may be accessed through other screens interlinked with the medical history and vital statistic information screens via the pointers in the tables associated with these interlinked screens. Past medical histories are typically recorded by a nurse or other medical practitioner in a medical clinic. To insure proper medical care, a physician will usually need to know a patient's past medical history in terms of diseases and past procedures performed. Medically significant habits for a patient, as well as the family history of disease, are also important to a physician.

FIG. 10 shows a preferred data entry and retrieval screen for family medical history associated with a specific patient. As with the patient's individual past medical history screen, the family history screen 112 includes a disease list 114 from which specific diseases may be selected to be associated with a relative. Associated with screen 112 is the Family History table 326 ("Family_Hist") (shown in FIGS. 21–24) in the relational database. Text entry areas for entering a relative's name 118 in relation 116 may be used by the medical practitioner to enter in the names and relationships of family members and any associated past disease or illness. The resulting information for the relatives of a patient are shown in parallel charts 120 at the bottom of the family history screen 112.

FIG. 11 illustrates a patient history screen having a past medical history display 100 and habits display 102. Each of these screens is associated with a Procedure History ("Proc_Hist") table 358 and a "Habits" table 334, respectively. Associated with the Procedure History table 358 is a Diagnosis History table 312 ("Diag_Hist") (tables shown in FIGS. 21–24). Each of these tables is associated with a list table to provide a customized list of procedures or diagnoses. In particular, the "Custom_P List" table 310 and the "Custom_D List" 308 are associated with the above history tables, respectively. The past medical history segment of the screen 102 preferably permits a user to view past diseases in a disease list 104 (associated with the Diagnosis History table 312) that displays diseases previously suffered by the patient in terms of date and disease name. To aid the user in selecting and entering diseases in the past medical history list a possible disease list 106 associated with "Custom_D List" 308 is available for use within the past medical history display 100. As a user types in a particular illness or surgery in a dedicated text box 108, a type-ahead function will display diseases on the disease list 106 as more characters are typed into the text box 108. A date entry box 110 is also positioned on the past medical history screen to associate the selected illness or surgery with a particular date after which the user may add or remove the selected illness or procedure to the disease list. The patient's habits display 102 is broken down into separate text entry areas for typical medically significant habits such as smoking, coffee drinking, alcohol consumption and exercise habits. Family history is also important in any physician's diagnosis of a patient.

Once the patient's medical history background has been updated or entered, a nurse attending to the patient prior to the physician's examination will record the patient's vital signs. A nurse, or other medical practitioner, may enter the vital statistics on a vital statistic entry screen 122 as shown in FIG. 12. This screen is identical to that shown in FIG. 16C, but reproduced at this point in the program to increase speed. The vital statistics, which will be stored in "Vitals" table 378 (shown in FIGS. 21–24) by patient name and date, include height 124, weight 126, temperature 128, pulse 130 and respiration 132. Text entry areas for blood pressure measured supine 134 and sitting 136 are also included. The nurse can also enter a patient's chief complaint in a text box 138 to update and clarify any earlier provided reasons for the visit that were recorded in the appointment scheduling screens at that time the patient made the appointment. The nurse will also review any drug allergy or other allergy information that the patient is aware of and enter those in dedicated text areas 140, 142 on the vital statistics interface 122.

Figure 13:
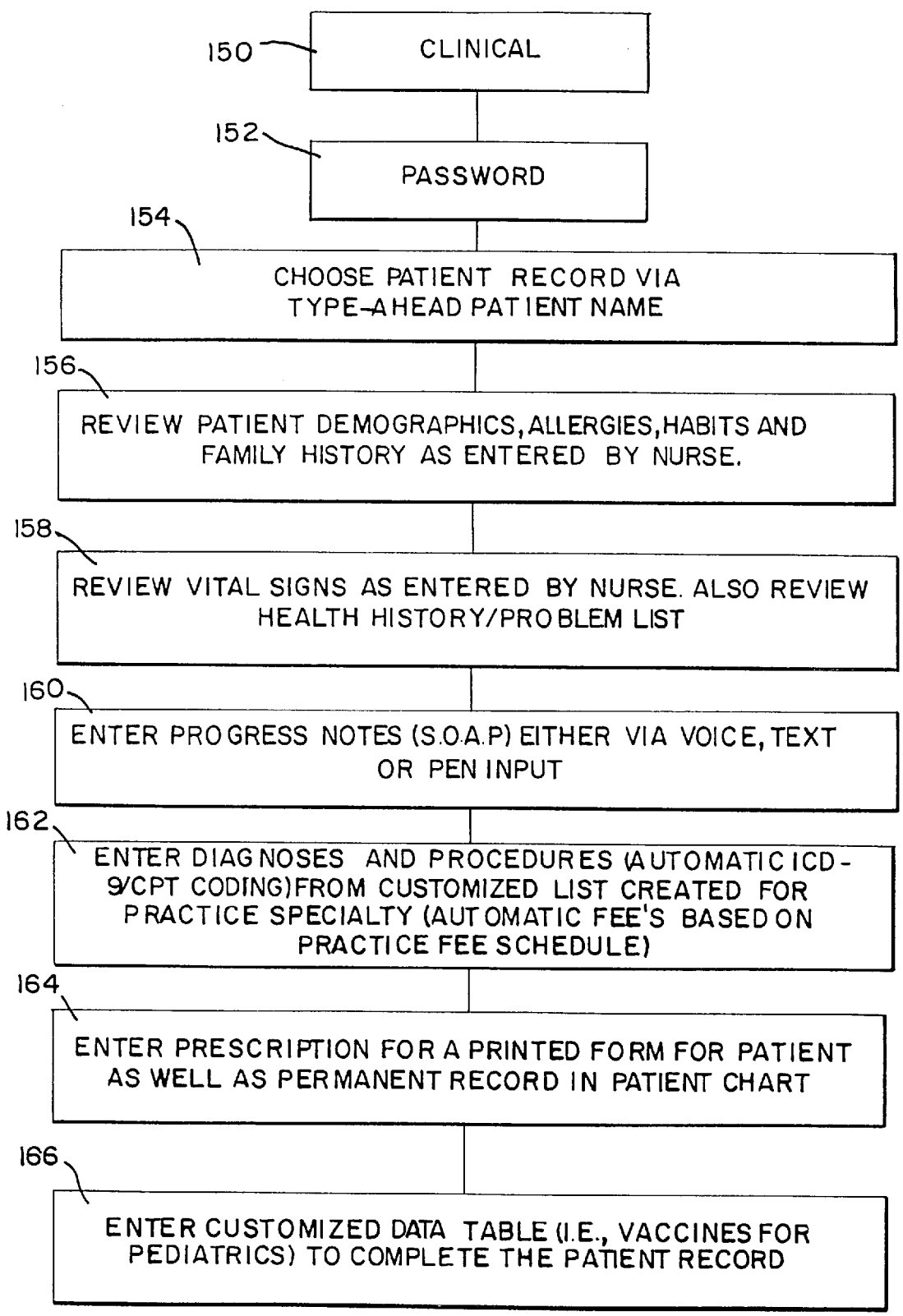
FIG. 13 is a flow chart illustrating a preferred method of managing patient information during an examination.

An important aspect of the presently preferred method is the ability for a physician to use a work station 14, either fixed or portable, to enter data, view patient history, and record diagnoses during the examination. At the beginning of the day when using a portable work station 14, or at a fixed work station in a examination room prior to a specific examination, a physician may select from the main menu screen 28 a clinical button 34 to access the clinical examination module. As best shown in FIG. 13, the physician first accesses the clinical module and then enters a password (at steps 150, 152). The password requirement ensures that only the proper personnel have access to patient information at the level permitted in the clinical module. After entering the password, the display 24 on the work station 14 produces a patient record screen through which the physician enters a patient's name to obtain the appropriate patient's information (at step 154).

After selecting the appropriate patient file history, the physician may review the patient's demographics, allergy, habits and family history information as previously entered by the nurse or other physician (at step 156). An allergy warning is displayed to the physician at each point in the clinical module. The physician may then select another screen to review the vital signs that were entered by the nurse and also review the health history and problem list relating to this specific office visit (at step 158). The physician may revise or update any of the information in the patient's file as is appropriate.

In a typical office visit, a physician will briefly review the patient history and vital signs as described above and then enter into the active portion of the examination, interviewing the patient and performing appropriate tests, procedures and measurements. An integral part of this process is recording progress notes during the examination or at the conclusion of the examination. According to a preferred aspect of the present invention, the physician may enter progress notes at the work station 14 choosing either voice, text or pen input modes (at step 160).

Preferably, the physician will enter his progress notes in a structured format including subjective observations as relayed to the physician from the patient, objective observations of the physician through the actual examination, assessment notes listing conclusions based on the subjective and objective observations, and a treatment plan. Following the basic examination and creation of progress notes, the physician may enter the diagnoses and procedures performed at the work station 14 (at step 162). The diagnoses and procedures may be listed and recorded using customized or automatic codes to aid in the billing process.

If a prescription is necessary as a result of is the visit, or to continue an ongoing prescription, the physician may enter a prescription at the work station 14 (at step 164). The step of entering a prescription may include selecting a drug and dosage from a table provided to the physician via the work station. The physician preferably enters prescription data into a preformatted form such that a permanent record may be created in the patient's file and a printed prescription form may be generated for the physician's signature. Additionally, the physician may wish to enter customized data relating to specific treatments, vaccines, or other tailored information (at step 166). All of this information, along with any information entered during the clinical visit via physician is preferably saved in the relational database temporarily stored in the workstation 14 memory 20 and more permanently maintained in the server 12. This information may be retrieved by patient identification information.

FIGS. 14–20 illustrate one preferred set of data entry and retrieval screens for use by the physician during the clinical examination as set forth in FIG. 13 above.

Turning now to FIG. 14, the physician may review the patient demographics, allergies, habits, and family history on a patient background screen 180. The patient background screen 180 is obtained by the physician through the patient selection screen 170 described above.

The patient's background screen in the clinical module displays to the physician all of the information the health care professional or nurse entered during the patient's initial consultation with the nurse just prior to the physician's examination, in addition to any previously obtained information. As described above, the patient information was entered in the past medical history display 100 and the family history display 112 described in FIGS. 10 and 11 above, and has been stored in various data tables associated therewith. The patient background screen 180 presented to the physician is for viewing only and is meant to refresh the physician's memory as to the patient's condition and recent treatment history.

The patient background screen 180, as well as all of the screens in the clinical module, displays an allergy alert if there are drug or other type allergies known for this patient. The allergies entered in the patient information module may be accessed from the main menu display 28 through the patient information button 32. This allergy information is stored by a patient identification number or other patient information in an "Allergies" table 304 (FIGS. 21–24). As the physician enters the clinical module to begin the examination process, the processor 22 in the work station 14 retrieves the allergy information entered for the patient from memory 20. Preferably, the word "allergy" flashes, in red letters, on the bottom of every screen in the clinical module to alert the physician of any existing allergies. The clinical module screens preferably display this allergy information for review only except for the new physical examination screen, discussed below, which allows additional input to maintain current patient allergy data.

The physician next reviews the vital signs earlier recorded by the nurse, including the patient's personal health history, on a vital statistics screen 190, shown in FIG. 15. The physician selects the vital signs screen button tab on the display to reach the vital statistics screen 190. Preferably, the vital statistics screen is a display only screen, showing the recent vital statistics of height, weight, temperature, pulse, respiration and blood pressure. A test result button 192 on the vital statistics screen permits the physician to quickly access any tests ordered or performed prior to the examination.

The patient's individual health history is displayed on a scrolling health history chart 194. Sorting command buttons 196 provide the physician with a simple way of sorting the health history by diagnosis or date to clearly show any health trends of the patients. The steps reviewing the patient's records and selecting the appropriate patient, reviewing demographics and vital signs shown in FIGS. 13–15 above, may be performed by the physician immediately prior to entering the examination room on a work station in the physician's office, may be accessed on a portable work station 14 that the physician carries, or may be found on the work station located in the examination room itself.

Preferably, the display-only screens described above are each associated with or read from the various data tables in the relational database. The screens can retrieve the particular information relating to a patient, for example, and display the information in an easy-to-read format.

As soon as the physician begins the physical examination of the patient, the physician will need to record progress notes. The physician may wish to record progress notes at the conclusion of the examination or as the examination progresses. FIG. 16 illustrates a preferred progress notes data entry and review screen 200. Preferably, the progress notes screen 200 allows a physician to enter notes on subjective material in a subjective text entry area 202, objective information in an objective text area 204, conclusions and diagnostics on an assessment text receiving area 206, and a treatment plan in a plan text entry area 208. Each of the text entry areas in the progress notes screen 200 is stored in a separate information table in the relational database cross-referenced to patient identification information, physician and date. For example, subjective text entry area 202 is associated with "SubName" table 372 and "Subjective" table 370, and objective text entry area 204 is associated with "Obj_Name" table 352 and "Objective" table 350 (shown in FIGS. 21–24). These progress notes are accessed through a Progress Notes Index table 362 ("Prog_Index"), a Progress table 364 ("Progress"), and a Follow-up notes table 330 ("Follow_Up_Notes"). The text receiving areas on the progress notes screen 200 all incorporate a conventional scrolling feature which permits a physician to enter extensive notes in each of these text receiving modes.

Multiple data entry techniques are usable with the progress notes screen of the presently preferred embodiment. Traditionally, physicians will enter their examination notes on pieces of paper or dictate more extensive notes after examination from shorthand notes made on paper during the examination. To facilitate the different note-taking styles of physicians, the presently preferred embodiment permits a physician to choose among several data entry devices to enter the notes. Before entering any information on the progress notes screen the physician preferably selects from a text button 210, a handwriting button 212, and a voice button 214, for indicating the type of data entry device desired.

When a physician selects the text button 210, data may be entered through a data entry device such as a standard keyboard or a computer pen. If a computer pen is used as a data entry device, the processor at the work station will recognize computer pen movement on the display and translate the handwritten characters into standard text. Suitable software for translating handwritten symbols into text is found in Visual Basic available from Microsoft Corporation. By selecting the handwriting button 212 on the progress notes screen 200, a physician can choose to enter the progress notes in his/her own handwriting such that the computer pen's movements are simply recorded in the physician's handwriting and not translated into block text. Selection of the handwriting button 212 informs the processor 22 that a special table of the digitized handwriting must be created in memory 20. Software is commonly available, such as Visual Basic available from Microsoft Corporation, for recording the digitized handwriting of a physician.

A physician selecting the voice button 214 alerts the processor 22 to accept voice input through a microphone as a data entry device 26. The physician can simply dictate notes into the microphone and the processor 22 will translate the electrical signals from the microphone corresponding to the physician's voice into text for display in the appropriate text area on the progress notes screen 200. One suitable software package form for entering the voice to text feature of the progress notes screen is Voice Type Dictation available from IBM Corporation. At the completion of the progress notes task, the physician saves the notes, and the processor 22 will direct the entered information into the appropriate data tables in memory 20.

The table information is stored by patient identification number, date and physician. By storing the information entered into the progress notes screen in the relational database, the physician can quickly recall and view past office visits with a patient and also may compare assessments and treatment plans for patients with similar ailments. The clear advantage of being able to search one or more patients' files to compare notes taken during an examination can greatly increase a physician's productivity and improve the diagnoses process. The multiple data entry methods permitted with the progress notes screen 200 in the presently preferred embodiment also insures that physicians with different note taking techniques will not be hindered or unduly interrupted by the data entry process.

With respect to the progress notes screen 200, as described above, subjective data is provided by the patient and is stored in a Subjective Data table 370 by patient identification, by date and time, and by physician. Objective data, determined by measurements and tasks performed by the physician, nurse, or laboratory, can be stored in the Objective Data table 350 for later retrieval and reference. As with subjective data, the objective data is stored by patient identification, by date and time, and by physician. The physician enters his assessment of the patient's condition in the assessment text entry area of the progress notes screen based on conclusions drawn from the subjective and objective entries. Treatment plan data includes any therapy, testing or medication regimens the physician determines is appropriate. As with the objective and subjective data, the assessment and plan data is stored for retrieval by patient identification, by date and time, and by physician for ease of retrieval and comparison.

A physician performing a routine physical examination that is unrelated to any new or ongoing illness may desire to skip the progress notes screen 200 by pressing the ADD PX button 201 to reveal a more structured physical examination recording screen as shown in FIGS. 16A–C. In the physical examination module of FIGS. 16A–C, the workstation presents a graphic user interface having overlapping folders containing subjective, objective and vital statistic information. As with the previously described screens, the recording screens can be associated with various tables in the database to store the input information.

As best shown in FIG. 16A, the physician may select an objective information screen 215 using the appropriate folder tab to reveal a predetermined list of examination areas in an examination list 216. Adjacent to each of the items in the examination list is a list of normal measurements 217, which can be either a simple yes/no determination or a customized measurement range. Also presented on the objective screen 215 is a comment area 218 adjacent to the list of normal measurements 217. Preferably, the work station 14 will only save information from the objective screen 215 for those items in the examination list where the physician entered information in the corresponding normal measurements 217 and comments 218 columns.

Selecting the subjective tab on the display reveals a subjective information screen 219 to the physician. A subjective criteria list 220 containing a predetermined area of inquiry list the physician should go through with the patient is positioned adjacent to a comment space 221 for receiving answers to questions the physician may pose to the patient concerning the areas of inquiry as well as general comments the physician may have. Typically, the subjective questioning will address the patient's subjective assessment of his/her health and personal activities such as exercise, sexual contact, substance use and so on. Again, the workstation will only save to memory those pieces of information from the subjective criteria list 220 where the physician entered comments in the corresponding comment space 221.

The physician also has access to the vital statistics recorded earlier by the nurse using the physical examination module of the presently preferred embodiment. Selecting the vitals folder tab reveals a vital statistics screen 222 that includes any and all of the standard measurements 223 taken by the nurse when the patient arrived for the appointment, such as blood pressure and pulse. A chief complaint region 224 displays any complaints the patient may have expressed to the nurse or physician. The physician enters or reviews drug or other allergy information through the allergy display 225 on the vital statistics screen 222.

After concluding an examination, the physician will often need to enter the diagnosis and procedures on a separate sheet of paper to initiate the appropriate billing sequence for the patients. According to the preferred embodiment of the present invention, a diagnosis screen 226 is available for the physician's use at the work station as shown in FIG. 17. The physician enters into the diagnosis/fee stage of an examination by selecting the diagnosis button on any of the available screens in the clinical module. The processor then provides the screen 226 for manipulation by the physician. Preferably, the diagnosis screen 226 includes a diagnosis table display 228 and a procedure table display 230 for recording the diagnosis procedure and the fee associated with the procedure. A database of diagnoses is available through a diagnosis list display 232 associated with a Custom Diagnosis table 308 ("Custom_D List" in FIGS. 21 and 24). In addition, a procedure list display 234 associated with a Custom Procedure table 310 ("Custom_P List" in FIGS. 21 and 24) is available for a physician to scroll through and select the appropriate procedure performed.

Figure 18:
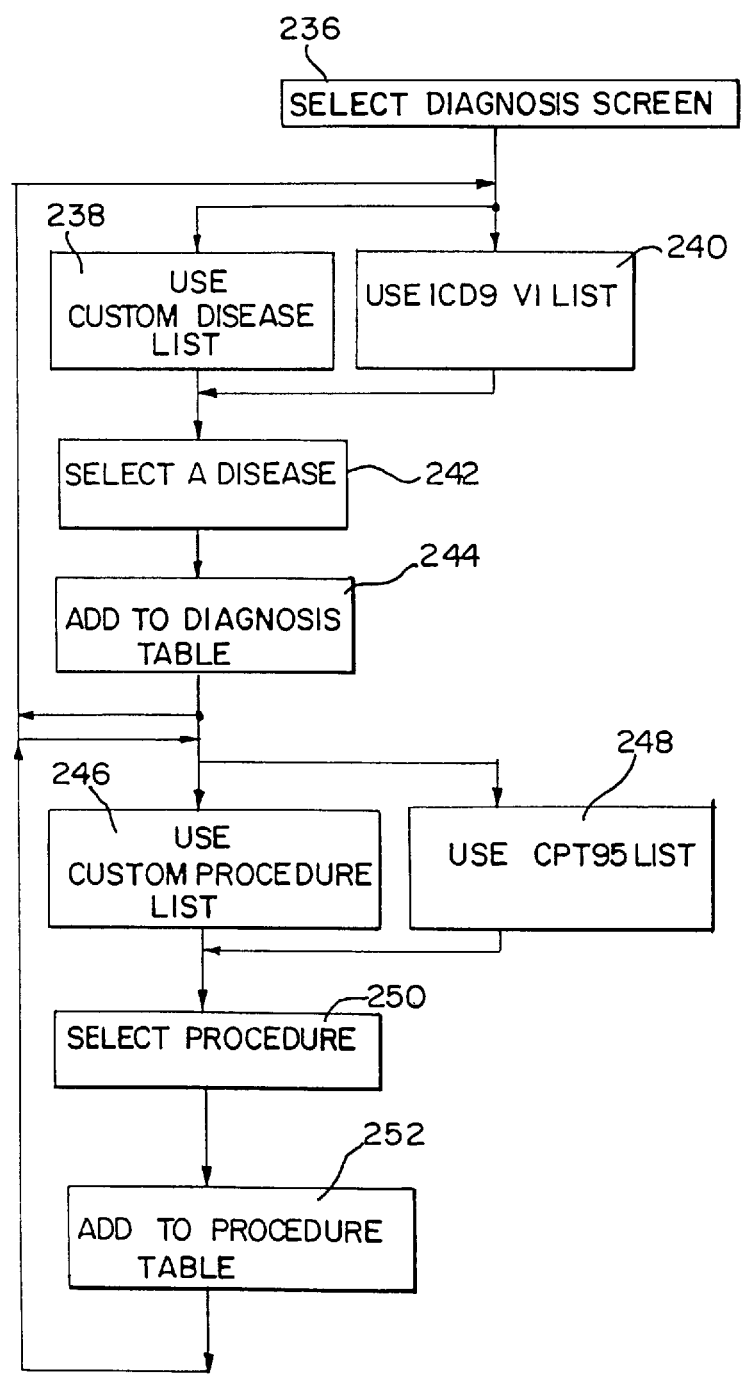
FIG. 18 is a flow chart illustrating a preferred method of recording diagnosis information.

The preferred method of selecting and completing a diagnosis using the diagnosis screen 226 on FIG. 17, is shown in FIG. 18. While in the clinical examination module, the physician first selects the diagnosis screen (at step 236). The physician may then either use the custom diagnosis display to scroll through and select the appropriate disease or other diagnosis or, may use a separate diagnosis code, or ICD9, list and use the appropriate disease/diagnosis code to retrieve the appropriate disease or diagnosis (at steps 238–240). "ICD9" is a database available from St. Anthony's Publishing Company. The database utilizes industry-accepted codes for various diagnoses. After viewing the custom diagnosis list or ICD9 list, the physician then selects a disease from the list provided (at step 242). The selected disease is then added to the diagnosis table list 308 that will be recording diagnosis for the visits (at step 244).

After selecting the disease, the physician has the option of choosing other diseases or diagnoses from the lists or continuing on to select the treatments or procedure from the custom procedure list 234 on the diagnosis screen 226 (at step 246). Alternatively, the physician can use a CPT 95 list, which is a database available from the American Medical Association. The database utilizes industry-accepted codes for various procedures (at step 248). The physician then selects the procedure viewed from the lists and adds the procedure to the procedure table list 230 (at steps 250–252). A predetermined fee is displayed in fee column 231 adjacent to the procedure list 230. Preferably the appropriate predetermined fee is associated with the selected procedures such that a patient bill may be easily and automatically generated after an office visit.

A physician will often need to write out a prescription for a patient at the end of an examination. Referring to FIG. 19, a preferred prescription data entry screen 254 is shown. The data entry screen 254 includes a medication entry portion 256, a refill instruction area 260, and a region for indicating for permission to use generic substitutes 258. An allergy alert screen 262 is always present on the prescription data entry screen 254 to alert the physician of potential or known allergies for the patient. The patient's actual allergies are preferably listed on the allergy alert screen 262. To assist the physician in selecting medications and instructions to provide a patient, a prescription data entry screen 254 preferably will include a medication "Dosage" table display 264 associated with Dosage table 322 and an "Instruction" table display 266 associated with the Instruction table 338 (shown in FIGS. 21 and 24), both of these tables pointing to the Prescription table 356 for the physician to scroll through and select medications, dosages, and instructions for including on the medication entry screen 256.

A physician may use a standard keyboard as the data entry device, or may use a computer pen to write in medications, dosages, and instructions. Physicians are not limited to using the predetermined dosages and instructions and may simply write in a prescription or edit an existing prescription called up from the associated dosage table 322 and instruction table 338 in the database. A physician's signature line 268 is also included on the prescription data entry screen for receiving the digitized physician signature to be entered through a computer pen or retrieved from a file. Upon completion of a prescription, the physician has the option of printing out or faxing to the pharmacy the completed prescription.

The clinical module used by physicians, according to the presently preferred embodiment, also provides for vaccine, lab or other customized data tables and displays. For example, a physician may select the vaccine folder within the clinical module to display the vaccine record display 270 and enter particular customized vaccination information into the "Vaccine" table 376 (shown in FIGS. 21–24). Also, laboratory reports displays may be generated as shown in FIG. 20A to compile reports of lab results in various configurations. The display shown in FIG. 20A may be associated with one or more of the lab-related tables 340–346 (shown in FIGS. 21–24).

As described previously, the information input from the various screens described above is stored in tables associated with the input screens. An alphabetical listing of the preferred table names is shown in FIG. 21. The relationships between these tables are established within the database to allow particular tables (and their associated screens) to "point" to other tables within the database. This pointing relationship allows the particular related tables to exchange or associate their information with each other through a database query. These table relationships are shown in FIGS. 22–24 of the drawings.

Turning now to FIG. 22, the relationships among the tables shown are represented by lines between individual tables. For example, the information relating to whether a particular physician is presently on or off call is contained in the "Doc_OnOff" table 316 and the availability of a particular physician is stored in the "Doctor_AvailTime" table 320. Each of these tables points to the "Appointments" table 302 and the "Cancel_Apmts" table 306, allowing tables 316 and 320 to associate with tables 302 or 306, which contain information regarding scheduled appointments or cancelled appointments, respectively. Tables 302 and 306 in turn point to User Information table 374, Patient Information table 354, and Insurance Information table 336. Thus, when a user can retrieve a particular appointment time from table 302, and at the same time retrieve information about the patient through table 354 and information regarding the particular patient's insurance through table 336. The remaining illustrated relationships are preferably as shown in FIG. 22.

The tables and relationships for the patient information screens shown in FIGS. 5–7 are shown in FIG. 23. As shown by the pointing relationships between the Patient Information table ("Patient_Infor") 354 and the radially outlying tables 304, 332, 326, 334, 336, 378, 312 and 324. The Patient Information table 354 thus points to several other tables, thus allowing a variety of types of information to be retrieved by patient information such as patient name or number. The Diagnosis History table 312 also points to Diagnosis List 308, which allows the diagnosis history screen to retrieve the customized list of particular diagnoses listed in table 308. Similarly, the Vitals table 378 points to the User Information table 374, allowing access to the information contained in table 374 from the Vitals screen.

Figure 24:
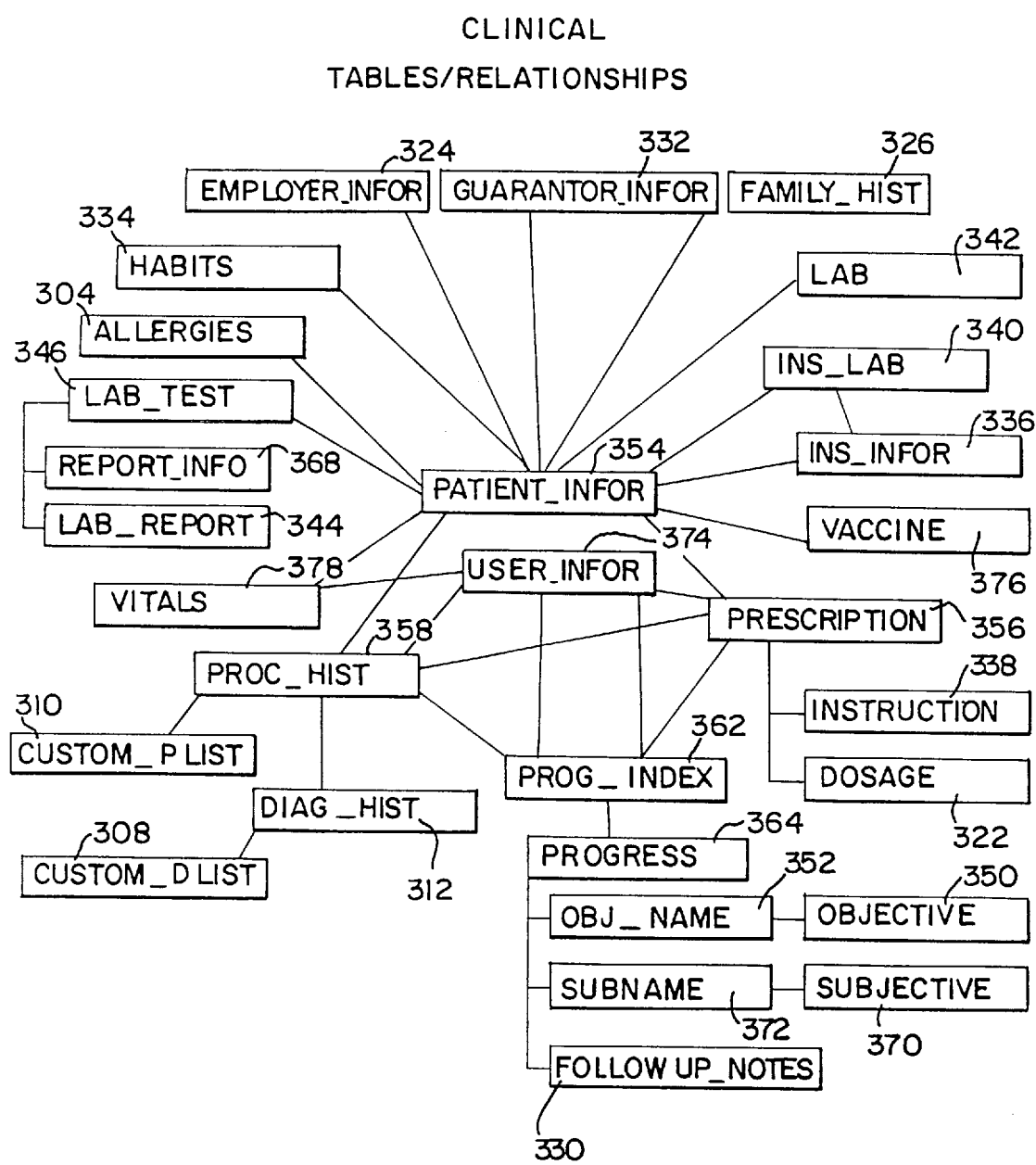
FIG. 24 is a map of the relationships among various database tables in the clinical module.

FIG. 24 illustrates the relationships among tables in the clinical screens described in FIGS. 13–20. Most of the relationships illustrated in the top half of FIG. 24 are explained in the discussion of Patient Information relationships of FIG. 23 above. As can be seen in FIG. 24, lab test information contained in table 346, which points to Lab Information table 368 and Lab Report table 344, points to Patient Information table 354, allowing retrieval of the lab information contained in tables 346, 368 and 344 via the patient information screens. The insurance information relating to labs and other insurance information contained in tables 340 and 336 are also linked to the Patient Information table 354 and to each other.

In the lower half of FIG. 24, the Procedure History table 358, the Prescription table 356, and the progress table 362 have pointing relationships with each other. This allows, for example, information on progress to be retrieved from the prescription information screens, or for procedure history to be retrieved from the progress screens. These tables 358, 362, and 356 also point to the User Information Table 374 and Patient Information table 354. As shown in the figure, the Procedure History table 358 also points to a Custom Procedure list 310 and the Diagnosis History table 312. The Diagnosis History table 312 also points to the Custom Diagnosis table 308. The Progress table 362 is actually an index of information which points to and allows access to the related progress notes tables 364, 352, 350, 372, 370 and 330. Finally, the Prescription table 356 points to both the Prescription Instruction table 338 and the Prescription Dosage table 322.

The relationships among these various tables are exemplary, and other relationships may be established by pointing between other tables, or creating new tables and displays, as the programmer desires.

The data contained in the database described above, preferably within the tables shown in FIGS. 21–24, can allow the user to access and analyze patient data in a variety of ways. In particular, the information previously gathered and stored in the database can be analyzed or compiled to track the effectiveness of treatments or medications on particular illnesses and the reasons therefor. Furthermore, patterns of diseases or symptoms may be tracked within a given geographical area or group of patients. The user can also identify trends in patient load and schedule in order to maximize the efficiency and effective use of the physician's time.

These various analyses may be accomplished via user screens similar to those described previously. For example, the user can choose an item (such as a table or a group of tables) and "drag" the item to a place on the screen and "drop" the item onto various icons representing processing options. The program would determine the hierarchy of the data chosen and group the data to generate data queries. The compiled data could then be printed into report format for use outside of the system.

From the foregoing, a comprehensive system and method for managing patient medical information in a medical clinic or physician's office has been described. The system includes at least a computer having a processor, memory, data input device and display capable of receiving, manipulating and displaying medical information. A common graphic user interface allows authorized users to manage medical information and provides physicians with a useful diagnostic tool to assist in examination and diagnosis of patients. Additionally, a method of managing, storing, recording and displaying patient medical data has been described that includes scheduling appointments, obtaining patient background information, retrieving, recording and displaying patient examination information, generating billing materials, generating analysis reports and generating prescriptions.

It is intended that the foregoing detailed description be regarded as illustrative rather than limiting, and that it be understood that the following claims, including all equivalents, are intended to define the scope of this invention.

We claim:

1. A computer aided method for creating, managing, updating, and analyzing patient information in a medical database to assist in the efficient operation of a medical clinic, the method comprising the steps of:

scheduling patient appointments and storing the appointments in a relational database;

compiling patient data, the data including at least one of medical history and demographic information, in the relational database;

displaying patient data compiled in the database to a user;

displaying an allergy warning to the user during a patient office visit;

updating patient data with progress notes concurrently with an examination of the patient during the patient office visit wherein the user records the progress notes into the relational database; and recording a diagnosis based on the progress notes.

2. The method defined in claim 1, wherein the step of displaying patient data to a user further comprises the steps of requesting a password from the user for access to patient data and selecting patient data for a particular patient by entering patient identification information.

3. The method defined in claim 2, wherein the step of displaying patient data further comprises the steps of selecting and reviewing at least one of demographic information, habit information, family history information and vital statistics information for the particular patient.

4. The method defined in claim 1, wherein the step of compiling patient data further comprises:

questioning a patient for personal information concerning at least one of the patient's insurance coverage, demographics, allergies, family medical history and habits;

recording the personal information into the relational database via a graphic user interface;

measuring the patient's vital statistics; and recording the measured vital statistics into the relational database via the graphic user interface.

5. The method defined in claim 1, wherein the step of scheduling appointments comprises scheduling an appointment by selecting a desired physician; displaying available appointment times for the selected physician; and selecting an available appointment time for an appointment.

6. The method defined in claim 1, wherein the step of scheduling appointments comprises:
scheduling an appointment by selecting a desired office location;
displaying available appointment times for the selected office location; and
selecting an available appointment time for an appointment.

7. The method defined in claim 1, wherein the steps of displaying patient data and allergy warnings to a user further comprise:
selecting a particular patient;
retrieving patient data for the selected patient;
selecting a particular portion of the retrieved data to display on a computer display device;
scanning the retrieved data for any allergy information; and
displaying an allergy warning for the patient concurrently with the particular portion of retrieved data on the computer display device.

8. The method defined in claim 7, wherein the step of displaying an allergy warning comprises flashing an alphanumeric warning on the computer display device.

9. The method defined in claim 1, wherein the step of updating patient data progress notes further comprises selecting a desired data entry format from a group of predetermined data entry formats via a graphic user interface on a computer display device.

10. The method defined in claim 9, wherein the step of selecting a desired data entry format comprises selecting a voice-to-text format for accepting dictated progress notes via a microphone and dictating patient data progress notes into the microphone.

11. The method defined in claim 1, wherein the step of displaying patient data to a user further comprises the step of selecting patient data for a particular patient by entering patient identification information.

12. A medical information system for managing patient medical history and examination data comprising:
a processor;
a display in communication with the processor;
a memory in communication with the processor for storing and manipulating patient data;
an input device in communication with the processor for receiving patient data;
said processor having:
patient identification means for responding to information entered at the input device and accessing a particular patient's datafile from the memory;
patient examination means for receiving and displaying patient data to a user during an office visit; and
wherein the patient examination means further comprises means for translating voice dictated information into textual information for storage in the memory, whereby the user may dictate patient data while examining the particular patient during the office visit.

13. The medical information system of claim 12 wherein the patient examination means comprises allergy warning means for retrieving allergy information from the memory for the particular patient and displaying an allergy warning on the display, the allergy warning means comprising an alphanumeric indicator positioned in the display.

14. The medical information system of claim 12 wherein the patient examination means comprise allergy warning means for retrieving allergy information from the memory for the particular patient and displaying an allergy warning on the display, the allergy warning means comprising a flashing alphanumeric indicator positioned in a bottom portion of the display.

15. A medical clinic computer system for collecting and analyzing patient examination data comprising:
a processor;
a display in communication with the processor;
a memory in communication with the processor for storing and manipulating patient data;
an input device in communication with the processor for receiving patient data;
said processor having:
patient appointment scheduling means for recording and displaying patient appointments;
patient background information means for storing and displaying at least one of patient demographic data, health history, family history and current vital statistics;
clinical analysis means, in communication with the patient background information means, for allowing a user to input and display diagnosis and progress data;
physician report summary means for displaying information on patient visits for at least one physician using the medical clinic computer system; and
communications utilities means for receiving and displaying laboratory reports; and
wherein the input device is a speech-to-text translation device, the speech-to-text translation device having a microphone for receiving speech information and translation means responsive to the received speech information for producing alphanumeric text corresponding to the received speech information and displaying the alphanumeric text on the display.

16. A medical clinic computer system for collecting and analyzing patient examination data comprising:
a processor;
a display in communication with the processor;
a memory in communication with the processor for storing and manipulating patient data;
an input device in communication with the processor for receiving patient data;
said processor having:
patient appointment scheduling means for recording and displaying patient appointments;
patient background information means for storing and displaying at least one of patient demographic data, health history, family history and current vital statistics;
clinical analysis means, in communication with the patient background information means, for allowing a user to input and display diagnosis and progress data, wherein the clinical analysis means further comprises prescription pad means for receiving patient prescription information input from the input device, the prescription pad means in communication with a dosage table containing a plurality of medications and dosages, the prescription pad means also in communication with a prescription memory for storing a prescription with a patient identification, a time stamp, and a physician name;
physician report summary means for displaying information on patient visits for at least one physician using the medical clinic computer system; and communications utilities means for receiving and displaying laboratory reports.

17. A graphic user interface, the graphic user interface displayed on a computer display device, for use in storing and retrieving patient medical information held in a database, the graphic user interface comprising:

a main menu screen having a plurality of function buttons for selecting one of a predetermined number of patient medical information screens, the function buttons comprising appointment, patient information, clinical, and report buttons;

an appointment screen accessible via the appointment button;

a patient information interface accessible via the patient information button;

a clinical examination interface accessible via the clinical button; and a reports screen accessible via the reports button.

18. The graphic user interface of claim 17, wherein the appointment screen comprises a patient identification region, a physician selection region, a location selection region, a month display region and a daily appointment time region.

19. The graphic user interface of claim 17, wherein the patient identification interface comprises a plurality of overlapping folders, each folder representing a different display screen and having a folder tab displayed for selection of a desired folder, the plurality of overlapping folders comprising:

a patient identification screen for recording patient identification information;

a patient insurance information screen having patient insurance information;

a patient employer information screen;

a patient past medical history and habit information screen;

a family past medical history screen; and a vital statistics screen for entering a patient's current vital statistics.

20. The graphic user interface of claim 17, wherein the clinical examination interface further comprises a general examination screen having a plurality of input format buttons and a plurality of text input regions, and a physical examination screen having a plurality of text input regions.

21. The graphic user interface of claim 20, wherein the input format buttons comprise a handwriting button, a text button, and a voice button for selecting a desired input method whereby a user may record examination data into a memory via the clinical examination interface using a selected input method.

22. The graphic user interface of claim 20, wherein the plurality of text entry regions on the general examination screen further comprise:

a subjective information text region for information provided to a user by a patient concerning health status;

an objective information text entry region for information gathered by a user through observing and testing the patient;

an assessment information text entry region for recording the user's conclusions and hypothesis; and a plan information text entry region, for recording a proposed treatment plan addressing the patient's needs.

23. The graphic user interface of claim 22, wherein each of the text entry regions includes a text scroll bar whereby the text entry regions may be viewed simultaneously on a single display screen.

24. The graphic user interface of claim 20, wherein the physical examination screen of the clinical examination interface further comprises an objective information entry region, a subjective information entry region, and a vital statistics entry region.

25. The graphic user interface of claim 24, wherein the subjective, objective, and vital statistic entry regions comprise overlapping folders, each folder having a separate screen display accessible via a folder tab continuously visible on the physical examination screen.

26. The graphic user interface of claim 17 wherein said appointment screen is associated with an appointment table, said patient information interface is associated with a patient information table, and said clinical examination interface is associated with a progress table.

27. The graphic user interface of claim 26 wherein said appointment table comprises a pointer pointing to said patient information table.

28. The graphic user interface of claim 27 wherein said progress table comprises a pointer pointing to said patient information table.

29. A memory having stored therein a plurality of tables for storing medical information, said tables comprising:

a user information table;

a procedure history table;

a vital information table;

a prescription table; and a patient information table;

said patient information table pointing to at least said vital information table, said prescription table and said procedure history table;

said user information table pointing to at least said prescription table, said procedure history table and said vital information table; and said procedure history table pointing to at least said prescription table, said user information table and said patient information table.

30. The memory of claim 29 wherein said user information table further comprises information relating to a particular computer user.

31. The memory of claim 30 wherein said procedure history table further comprises information relating to a compilation of medical procedures.

32. The memory of claim 31 wherein said vital information table further comprises information relating to a compilation of vital signs.

33. The memory of claim 32 wherein said prescription table further comprises information relating to at least one medical prescription order.

34. The memory of claim 33 further comprising a progress table, said progress table associated with at least said prescription table and said procedure history table.

35. The memory of claim 34 wherein said progress table further comprises information relating to a compilation of evaluations regarding one or more patients.

36. The memory of claim 29 further comprising a diagnosis history table, said diagnosis history table pointing at least said procedure history table.

37. The memory of claim 36 wherein said diagnosis history table further comprises information relating to a compilation of medical diagnoses.

38. The memory of claim 37 further comprising a custom diagnosis list table, wherein said diagnosis history table points to said custom diagnosis list table.

39. The memory of claim 38 wherein said custom diagnosis list table further comprises a compilation of standard medical diagnoses.

40. A database having stored therein a plurality of tables for storing medical information, said tables comprising:

a procedure history table;

a prescription table; and a progress table;

said procedure history table pointing to at least said prescription table and said progress table, said prescription table pointing to said procedure history table and said progress table, and said progress table pointing to said procedure history table and said prescription table.

41. The database of claim 40 wherein said procedure history table further comprises information relating to a compilation of medical procedures.

42. The database of claim 41 wherein said prescription table further comprises information relating to at least one medical prescription order.

43. The database of claim 42 wherein said progress table further comprises information relating to a compilation of evaluations regarding one or more patients.

44. The database of claim 40 further comprising a diagnosis history table, said diagnosis history table pointing to at least said procedure history table.

45. The database of claim 44 wherein said diagnosis history table further comprises information relating to a compilation of medical diagnoses.

46. The database of claim 40 further comprising an allergies table and a patient's information table, said allergies table pointing to said patient information table, and said procedure history table, said prescription table, and said progress table pointing to said patient information table.

47. The database of claim 46 wherein said allergies table further comprises information relating to allergic reactions, and said patient information table further comprises personal information relating to one or more particular patients.

48. A method of analyzing tables in a database, said method comprising the steps of:

providing a procedure history table including information relating to a compilation of medical procedures, a prescription table including information relating to at least one medical prescription order, and a progress table including information relating to a compilation of evaluations, said procedure history table pointing to at least said prescription table and said progress table, said prescription table pointing to said procedure history table and said progress table, and said progress table pointing to said procedure history table and said prescription table;

retrieving said information from at least one of said tables;

associating said information from said at least one of said tables with information from another of said tables to produce a screen of associated information; and displaying said associated information.

49. The method of claim 48 further comprising the step of printing said associated information.

* * * * *